United States Patent [19]
Hickok et al.

[11] Patent Number: 5,867,912
[45] Date of Patent: Feb. 9, 1999

[54] ADJUSTABLE SURGICAL HANDLE

[75] Inventors: Teresa R. Hickok, Bonita; Claude E. Martin, Chula Vista, both of Calif.

[73] Assignee: San Diego Swiss Machining, Inc., Chula Vista, Calif.

[21] Appl. No.: 855,737

[22] Filed: May 9, 1997

Related U.S. Application Data

[63] Continuation-in-part of Ser. No. 528,079, Sep. 14, 1995, Pat. No. 5,657,541.

[51] Int. Cl.⁶ ........................................................ B26B 5/00
[52] U.S. Cl. ................................. 30/329; 30/123; 30/337; 81/439; 279/46.4; 279/56; 606/167
[58] Field of Search .............................. 30/123, 329, 330, 30/337–339; 81/439; 279/46.4, 56; 606/162

[56] References Cited

U.S. PATENT DOCUMENTS

| | | | |
|---|---|---|---|
| D. 324,475 | 3/1992 | Staubitz et al. ............................ | D8/99 |
| 2,022,775 | 12/1935 | Holland-Letz ............................. | 145/62 |
| 2,569,286 | 9/1951 | Bunker ...................................... | 30/329 |
| 2,635,491 | 4/1953 | Bell et al. .................................. | 80/5.1 |
| 2,933,955 | 4/1960 | Laemmel .................................... | 80/6 |
| 3,922,784 | 12/1975 | Prince et al. .......................... | 30/329 X |
| 4,496,163 | 1/1985 | Bernfeld .................................. | 279/1 A |
| 4,617,816 | 10/1986 | Brinkman .................................. | 72/104 |
| 4,788,976 | 12/1988 | Dee ......................................... | 606/167 |
| 4,969,231 | 11/1990 | Mader et al. ............................. | 16/141 |
| 5,055,106 | 10/1991 | Lundgren ................................. | 606/167 |
| 5,203,086 | 4/1993 | Dann ........................................ | 30/293 |
| 5,431,671 | 7/1995 | Nallakrishnan .......................... | 606/167 |
| 5,433,457 | 7/1995 | Wright ..................................... | 279/90 |

FOREIGN PATENT DOCUMENTS

2 201 362  9/1988  United Kingdom .

Primary Examiner—Douglas D. Watts
Attorney, Agent, or Firm—Baker & Maxham

[57] ABSTRACT

A handle assembly having a swivel head for detachably holding a blade, includes a substantially elongate handle having a proximal end and a distal end, the proximal end is formed with a threaded shank having a having a hemispherical socket at the end thereof, a sleeve having a threaded socket on one end for threadably mounting on the threaded shank and having an open slot extending from the other end to intersection of the threaded bore and partially along the length thereof, a blade mounting head comprising a threaded cylindrical body having a shank extending from one end, the shank adapted for receipt in the open slot and having a spherical tip for receipt in the threaded bore and engagement with the sleeve and the semi-spherical socket, the body adapted for swiveling on the spherical tip in the socket and slot, an axial bore extending coaxial of the threaded cylindrical body from the other end, an elongated collet having a longitudinal axis and inner walls surrounding an axial passage and first and second opposite ends, the collet having a first longitudinal slit extending from the first end for receiving a blade into the axial passage and forming a first set of jaws that are compressible for gripping opposing sides of the blade, the collet adapted for receipt in the axial bore, and an elongated retaining sleeve member having first and second opposite open ends and a longitudinal axis with a longitudinal inner bore, the retaining member threadably mounted on the head and being configured to secure the collet and apply a compressive force to the collet for gripping a blade transverse bore intersecting the threaded bore, at the open slot.

20 Claims, 6 Drawing Sheets

ADJUSTABLE SURGICAL HANDLE

BACKGROUND OF THE INVENTION

REFERENCE TO RELATED APPLICATIONS

The present application is a continuation-in-part of co-pending application Ser. No. 08/528,079, filed Sep. 14, 1995 and now U.S. Pat. No. 5,657,541 entitled HOLDER ASSEMBLY FOR SURGICAL BLADE, now allowed.

1. Field of the Invention

This invention relates generally to surgical instruments and more specifically to a surgical handle having an adjustable head for adjustably holding a surgical blade at selectable angles to the handle.

2. Description of the Related Art

In the aforementioned parent application, a unique handle or holder assembly for surgical blades with improved blade gripping jaws and blade cover/wrench is disclosed. The present invention is an improvement over the prior holder and addresses additional concerns in the art.

Surgical instruments, and in particular blades, are required to be extremely sharp in order to make incisions and the like. Unfortunately, the sharp instruments are a safety hazard to the people who use them. A cut to a doctor, nurse, or other medical personnel exposes the medical person to viruses and other infections that can enter the person's body through the open cut. Additionally, the cut may cause blood to contaminate the blade which exposes other persons, including patients, to the risk of exposure to these harmful contaminants.

Surgical tools and instruments must be sterile prior to use in order to reduce infection and transmission of disease. Surgical knives are expensive and hazardous to handle during sterilization. For this reason surgical knives are now typically constructed with disposable blades and reusable handles. This eliminates the blade during sterilization of the handle and enables the use of new fresh blades with each use.

One cause of injury by surgical tools is caused by a blade that is not securely held in place in its handle. Surgery tends to be very stressful on the cutting instrument due to odd cutting angles that are sometimes necessary and the force required to make an incision. Prior art surgical devices exhibit a tendency for the blade to be dislodged from its holder in such a situation. This has been largely solved by our above identified invention. The inventors of the present invention have made the critical recognition that a significant factor contributing to this problem is that prior art surgical instruments hold the blade secure in only one direction. Thus, a substantial force introduced in another plane on the blade may dislodge it from its handle.

In addition, the prior art fails to accommodate the odd angles at which the surgeon must work. Prior art holders are limited in the angle and orientation capabilities of the blade relative to the holder.

Another type of injury caused by sharp surgical blades occurs when they are being placed in or removed from their handles. Typically such blades are placed in a handle and a nut is tightened around a securing member to hold them in place. The nut is usually tightened with an open-end or boxed-end wrench. Any slippage by the operator, when tightening the nut, immediately exposes the operator to the risk of being cut by the sharp blade. A similar risk exists when the blade is being removed with such a wrench. There is a need for a wrench and blade handle assembly combination that allows for insertion/removal without exposing the operator to the risk of injury. Furthermore, such an advantage provided with a blade handle assembly that also prevents the slippage of such blades during operation and enables adjustment of the angle of the blade would be a significant advancement in the art.

Because of the risk of exposure to contaminants in human blood, described above, it is essential that all instruments used in surgical operations be cleaned thoroughly before being re-used. Since a wrench used to remove the blade may become contaminated it must be cleaned after use. However, the inventors have made the critical recognition that there is a need to somehow shield the operator from the blade during insertion/removal and a need for a simple and easy way to clean the wrench. Thus, there is an evident need in the art to provide apparatus with the advantages described above while enabling easy cleaning of the entire assembly including the wrench.

SUMMARY OF THE INVENTION

An objective of this invention is to provide an improved surgical blade holder that overcomes the problems described above.

In accordance with a primary aspect of the present invention, a handle assembly having a swivel head for detachably holding a blade, comprises a substantially elongate handle having a proximal end and a distal end, said proximal end is formed with a threaded shank having a hemispherical socket at the end thereof, a sleeve having a threaded socket on one end for threadably mounting on said threaded shank and having an open slot extending from the other end to intersection of said threaded bore and partially along the length thereof, a blade mounting head comprising a threaded cylindrical body having a shank extending from one end, said shank adapted for receipt in said open slot and having a spherical tip for receipt in said threaded bore and engagement with said sleeve and said semi-spherical socket, said body adapted for swiveling on said spherical tip in said socket and slot, an axial bore extending coaxial of said threaded cylindrical body from the other end, an elongated collet having a longitudinal axis and inner walls surrounding an axial passage and first and second opposite ends, the collet having a first longitudinal slit extending from the first end for receiving a blade into the axial passage and forming a first set of jaws that are compressible for gripping opposing sides of the blade, said collet adapted for receipt in said axial bore, and an elongated retaining sleeve member having first and second opposite open ends and a longitudinal axis with a longitudinal inner bore, the retaining member threadably mounted on said head and being configured to secure the collet and apply a compressive force to the collet for gripping a blade transverse bore intersecting said threaded bore, at said open slot.

BRIEF DESCRIPTION OF THE DRAWING

The objects, advantages and features of the present invention will be more clearly understood by reference to the following detailed disclosure when read in conjunction with the accompanying drawing, in which.

DETAILED DESCRIPTION OF THE PREFERRED EMBODIMENT

This invention is described with reference to a preferred embodiment shown in the drawing figures. In these figures, a like number shown in various figures represents the same or similar elements in each figure. While this invention is described in terms of the best mode for achieving this invention's objectives, it will be appreciated by those skilled in the art that variations may be accomplished in view of these teachings without deviating from the spirit or scope of the invention.

Handle Assembly Overview

Figures 1, 2, 3, 4, 5:
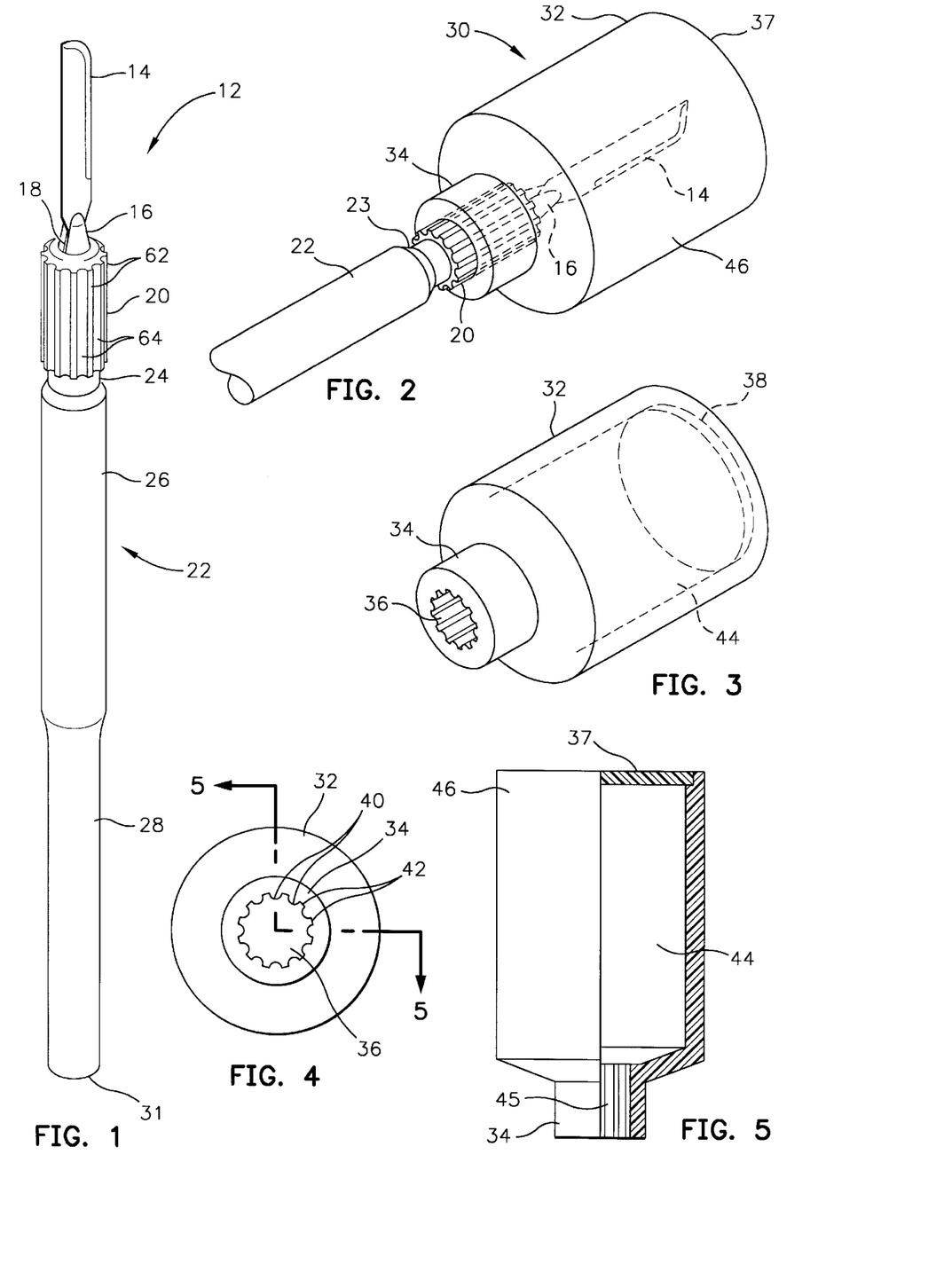
FIG. 1 is a perspective view of the handle assembly of the present invention holding a blade having opposing sides and opposing edges.
FIG. 2 is an isometric view of a wrench for securing and loosening the retaining member of the handle assembly of FIG. 1 shown engaging the retaining member attached to the handle member of the handle assembly of FIG. 1.
FIG. 3 is an isometric view of the wrench of FIG. 2 with the handle assembly removed and a hidden view of the removable insert of the wrench shown.
FIG. 4 is a top plan view of the wrench of FIGS. 2 and 3 showing the open end for receiving the retaining member and blade of FIG. 1.
FIG. 5 is a partial sectional side view taken along line 5—5 of the wrench shown in FIG. 4.

FIG. 1 shows handle assembly designated generally by the numeral 12 for holding a blade 14 in a secure safe position. As will be described in detail below with reference to FIG. 7, the collet 16 holds the blade 14 secure in two directions gripping both opposing sides and opposing edges of the blade. Such a safe securing operation has not been achieved by the prior art and this is a novel non-obvious aspect of this invention. The collet 16 has a longitudinal slit 18 extending from one end of the collet for receiving the blade. When the collet 16 is compressed the opposing walls formed by slit 18 clamps down on the blade 14 and this provides one of the securing forces on the blade. The retaining nut or member 20 is used to tighten the collet and apply the compressive forces which allow the collet to hold the blade in place. The collet fits in an opening in the handle 22 and is secured by retaining member 20. Twisting the retaining member compresses the collet 16 and closes longitudinal slit 18 so that the blade is held in place. The handle member has a neck 24 near the first end which is open and a middle section 26 and a tapered portion 28 near the second end 31. It is not absolutely required that the portion 28 be tapered, i.e. of a smaller diameter than section 26. However, tapering this portion allows a portion of the handle to be thicker for a better grip for holding the blade while allowing some portion of the handle to be thinner so that it can be used in combination with a wrench member, described below, in order to remove a cap which fits over a normally closed end of the wrench.

Handle Assembly-Wrench Combination

Referring to FIGS. 2 and 3, a combined wrench and protective shield member 30 having an open end 36 and a closed end 37 is shown. FIG. 2 shows the wrench in operating engagement with the retaining member of the handle assembly which is in place on the neck portion of handle 22. The blade 14, held in place in the collet, is protectively contained or shielded within the axial passage 44 of the larger diameter portion 32 of the wrench 30. The blade is safely contained within the enclosure by cover 46. However, the blade can be safely loosened by wrench 30 for removal from handle 22 without exposing medical personnel to a sharp blade. The ability to loosen the blade or better secure it to the handle member without exposing the operator to the risk of an infection is believed to be a significant advancement in the art. A smaller cylinder portion 34 of the wrench body is configured to be able to apply a twisting force to retaining member 20. In turn this imparts a force on collet 16 and, in particular, compresses the longitudinal slits of the collet closer together to hold the blade firmly in place. Turning the wrench in an opposite direction loosens the retaining member 20, thereby allowing the longitudinal slits to expand and release blade 14.

FIG. 3 shows the opening 36 attached to the smaller cylinder portion 34 in which the retaining member fits to pass the blade into the axial passage of the wrench. At the second end 37 (FIG. 2) of the wrench a removable insert or cap 38 can be removed in order to allow cleaning of the axial passage 44 and the inside wall of cylindrical portion 34 which is configured to turn the retaining member 20. The cap is shown as a force-fit member, but it would be apparent to one skilled in the art to create threads on the cap and wrench member for allowing insertion and removal by a screwing action. This is a significant advancement in the art because it is important to clean any medical instrument which may have come into contact with blood due to the danger of contamination.

FIGS. 4 and 5 show the wrench 30 from a different point of view of that shown in FIG. 3. FIG. 4 is a top plan view of the wrench where opening 36 can be clearly seen. Ridges 40 and valleys 42, which are disposed between the ridges, are used for mating up with matching ridges 62 and valleys 64 (FIG. 1) on the retaining member 20 in order to twist the retaining member.

FIG. 5 shows a partial sectional view taken along sectional lines 5—5 of FIG. 4. In this view the cover 46 is partially removed to reveal the axial passage 44 and the inner wall 45 of the smaller cylindrical portion 32. In this view it will be appreciated that the end 37 is sealed by removable insert 38 so that the blade is not exposed. For safety's sake, it is important that the blade be prevented from jamming against the insert. This may be accomplished by shortening the length of the threaded portion of the smaller cylinder or by lengthening the longitudinal axis of axial passage 44.

Figures 6, 7, 10:
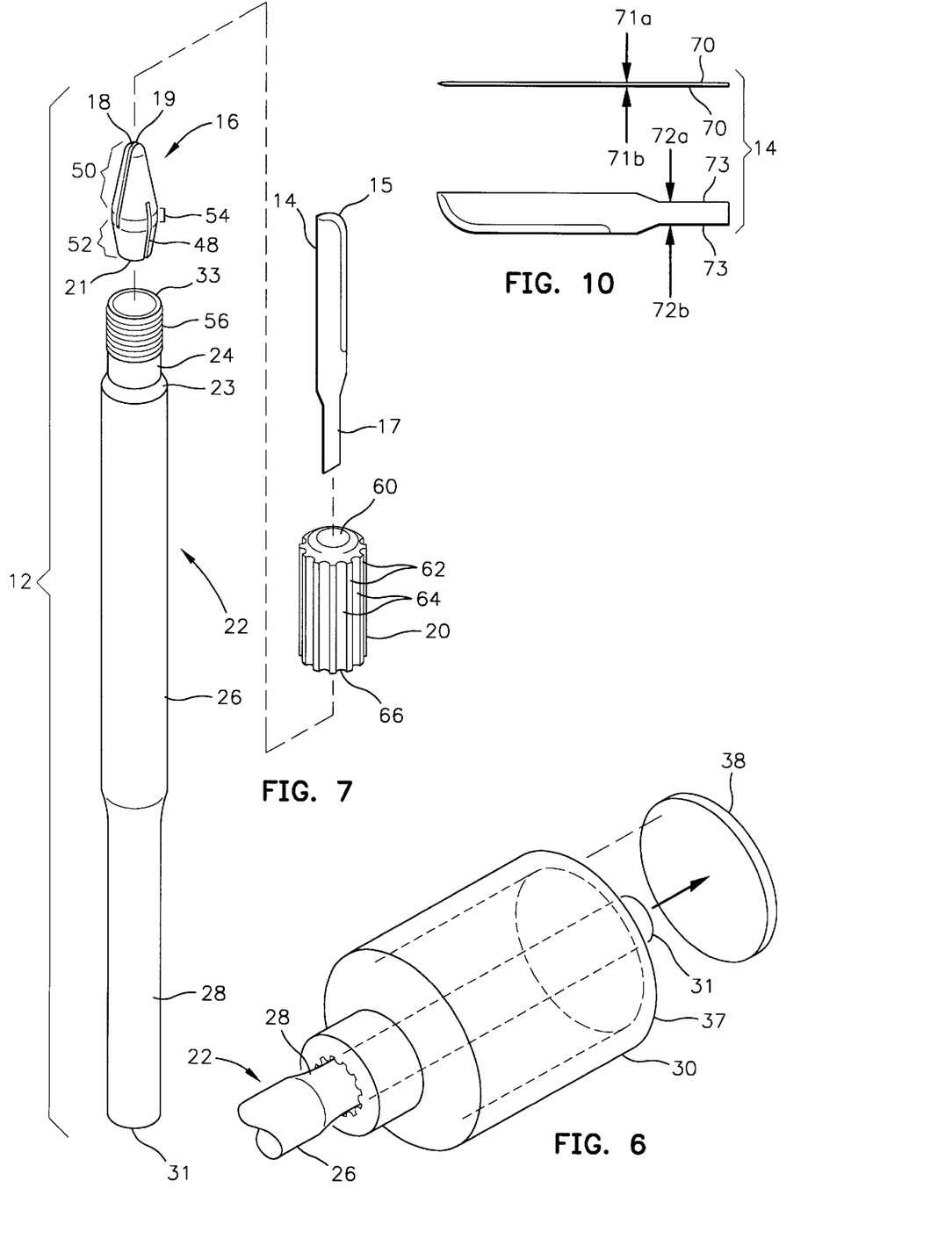
FIG. 6 is an isometric view showing the removable insert of the wrench being removed by the closed end of the handle of FIG. 1.
FIG. 7 is an exploded view of the handle assembly of FIG. 1 showing the handle, the collet, the retaining member, and a blade.
FIG. 10 shows opposing sides and opposing edges of the blade of FIG. 1 with force vector shown to indicate the securing compressive forces enabled by the longitudinal slits of FIG. 8 and FIG. 9 when the collet is placed in the handle and the retaining member is turned in a securing direction.

FIG. 6 shows handle 22 with tapered portion 28 inserted in the axial passage of wrench 30 wherein end 31 is capable of pushing removable insert 38 off of end 37 of the wrench so that the inside of the wrench can be cleaned. The cleaning may be done in two steps, first with a bottle brush and then placing the wrench member in a sterilizing apparatus.

FIG. 7 shows an exploded view of the handle assembly 12 described above with reference to FIG. 1. The handle 22 includes open end 33 for receiving the collet and opposite closed end 31. Between the open end and the closed end is a neck 24 including a threaded portion 56, shoulders 23 which is adjacent middle portion 26, and tapered end portion 28 which is adjacent the closed end. The threads mate up with corresponding threads 68 (FIG. 8) on the inside of the retainer 20. The middle portion 26 is preferably thick enough to allow a comfortable grip by an operator. The reduced portion 20 is preferred to be dimensioned to fit within the axial passage of the wrench in order to pop the removable inset out.

The handle assembly includes a collet 16 that has a substantially elongated body that is preferably conically shaped at each end. The conically shaped body has a first longitudinal slit 18 extending from one end of the collet to substantially the middle of the collet 54 forming a first pair of spaced opposed jaws. A second longitudinal slit 48 extends from an opposite end of the collet just past the middle portion 54 forming a second pair of spaced opposed jaws.

Preferably, the length of the slits overlap. Additionally, the slits should be offset at an angle from each other. In other words, each slit is offset at a different angle from the longitudinal axis. Preferably, each slit is offset at about ninety degrees from the other.

In a preferred embodiment, the conical shape is further divisible into two opposing cones sharing frustum sections through middle portion 54. The first conical section 50 has a tip at first end 19 and the oppositely oriented second cone 52 also has a frustum section in the middle 54 and has a somewhat truncated tip section at the end of the collet 21.

It is not necessary that the collet be conical in shape; however, the inventors have recognized that this is the best configuration for achieving the invention's objectives. The collet is preferably an elongated body having an axial passage from end 19 to end 21. The longitudinal slit 18 extends from end 19 to about the middle and receives the blade 14 into the axial passage of the collet. The opposing jaw or wall assembly formed by the longitudinal slit 18 is compressible by the retaining member at open end 60 so that the walls can be used to clamp or grip opposing sides of the blade. A second jaw or wall assembly formed by longitudinal slit 48 extends from the end 21 and is also compressible by the retaining member and serves to allow clamping or gripping by the inner walls of the collet of opposing edges of the blade. Thus, the blade is gripped in two directions to ensure that it does not slip or fall out.

The ability to grip the blade in two directions is a critical advancement in the art which has not been accomplished by the prior art. It is preferable to place the blade into the collet prior to tightening the retaining member 20. Typically such blades, as blade 14, are provided with protective sheathes over sharp portion 15 which can be used by a human to grip the blade safely prior to placing it in the collet. However, these sheathes are disposed of once the blade is installed the first time, and subsequent removals are rendered dangerous with prior art wrenches.

A shank portion 17 of blade 14 slips into longitudinal slit 18 through an axial passage in the collet body and through open end 21. Blade 14 and collet 16 enter the retaining member 20 through open end 60. The retaining member is turned and its internal threads secure it to threads 56. Open end 66 of the retaining member, when installed on the assembly, extends past the threaded portion 56 into the neck portion 24 of the handle 22. Conveniently, the ridges 62 disposed on either side of valleys 64 can be used to turn the retaining member between the fingers of an operator. This hand-tightening operation is safe to perform the first time the blade is installed but the inventors have recognized that it is unsafe to perform by regular medical personnel once the sheath has been disposed and therefore have provided the wrench member for the combination of this invention. Once a retaining member including a collet and blade is removed from the handle it can be left in the protective enclosure of the wrench handle. The wrench member can then be moved to a special area where special equipment such as pliers are available so that specially trained personnel may process the contaminated blade. Meanwhile, a new blade, collet, and retaining member can be installed on the handle for use in surgery.

Figure 8:
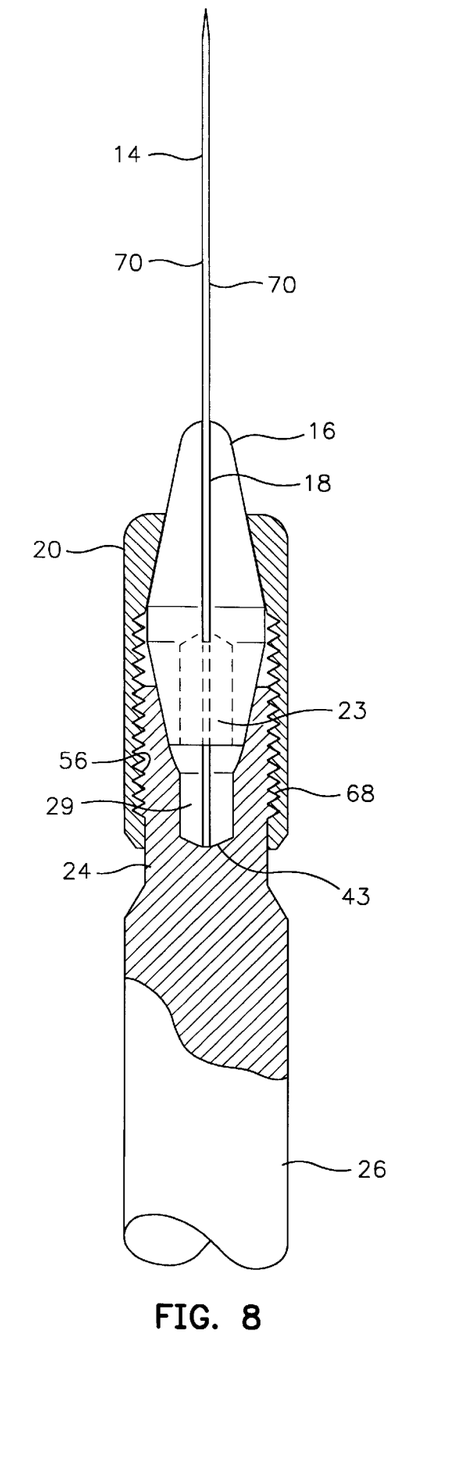
FIG. 8 is a partial sectional view of the collet secured in the handle by the retaining member and engaging a blade in a longitudinal slit.

FIG. 8 is a partial sectional view showing a portion of handle 22 with the collet in place in the threaded portion of the neck of the handle and the retaining member also in place. Blade 14 is held in place in longitudinal slit 18 by the compressing force of retaining member 20 as the retaining member's threads 68 engage the threads 56. A hollow portion 29 in the neck begins at wall 43 and extends to end 33. It is partially filled up by the collet. The collet has an axial passage which is composed of hollow portion 23 of the collet combined with the longitudinal slit 18.

Figure 9:
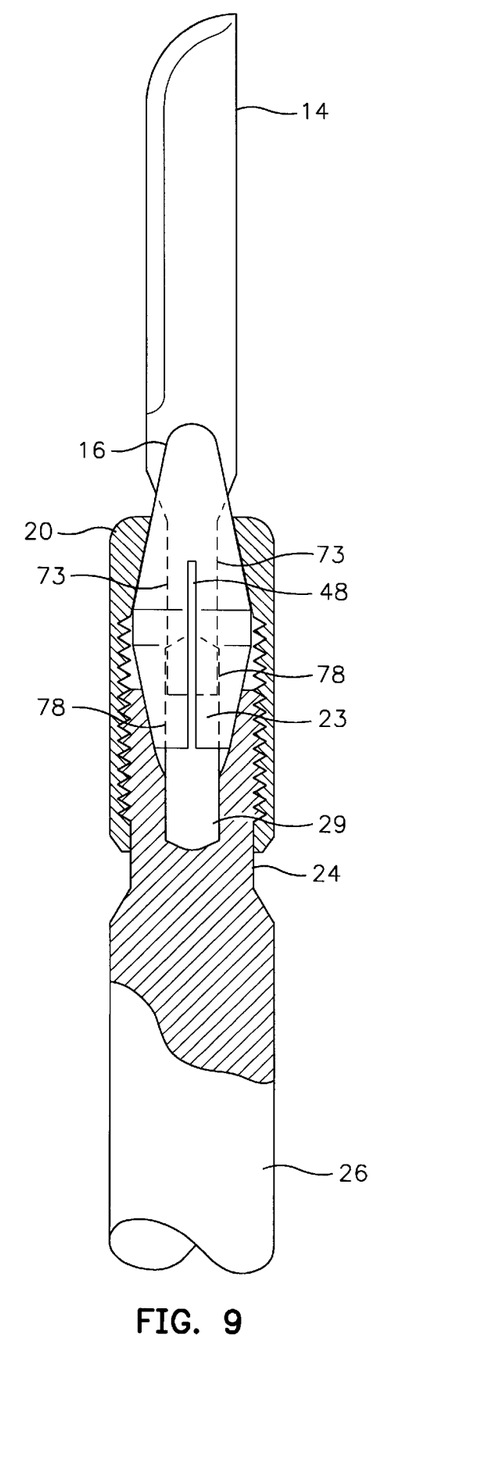
FIG. 9 is a partial sectional view of the collet, blade, retaining member and handle of FIG. 8 showing another longitudinal slit.

FIG. 9 shows a partial sectional side view of the handle, including middle portion 26 and neck 24, with the above-described threaded portion for mating with the threaded portion of the retaining member 20. When the retaining member is tightened the longitudinal slit 48 allows the inner walls 78 of the collet at hollow portion 23 to be compressed and clamped down on edges 73 of the blade 14. Thus, the blade is held in place by a securing compressive force on edges 73 as well as a securing compressive force in another direction on opposing sides 70 (FIG. 8). The longitudinal slits 18 and 48 allow the collet to be elastically deformable in response to a compressive force yielded by tightening the retaining member.

FIG. 10 shows a schematic representation of the compressive forces yielded by the collet on the blade 14. A compressive force in direction 71a and 71b on sides 70 is exerted by the compression of longitudinal slit 18. A compressive force in direction 72a and 72b on edges 73 is yielded when blade 14 is compressed by the retaining member.

Regarding composition materials, the inventors have determined that the following choices are the best for achieving the invention's objectives. The wrench is preferably made of a sterilizable plastic, e.g. ultem. The collet is preferably made of stainless steel because of the desirable elasticity of that metal. Empirical evidence has shown that it is best to heat-treat the steel to obtain about 40–14 42 C-scale Rockwell hardness. The retaining member and handle are preferably made of titanium because it is very strong but is also light-weight and non-corrosive. The handle is preferably solid from end 31 to neck 24 until it is necessary to create the hollow portion for receiving the collet.

Figures 11, 15, 16, 17:
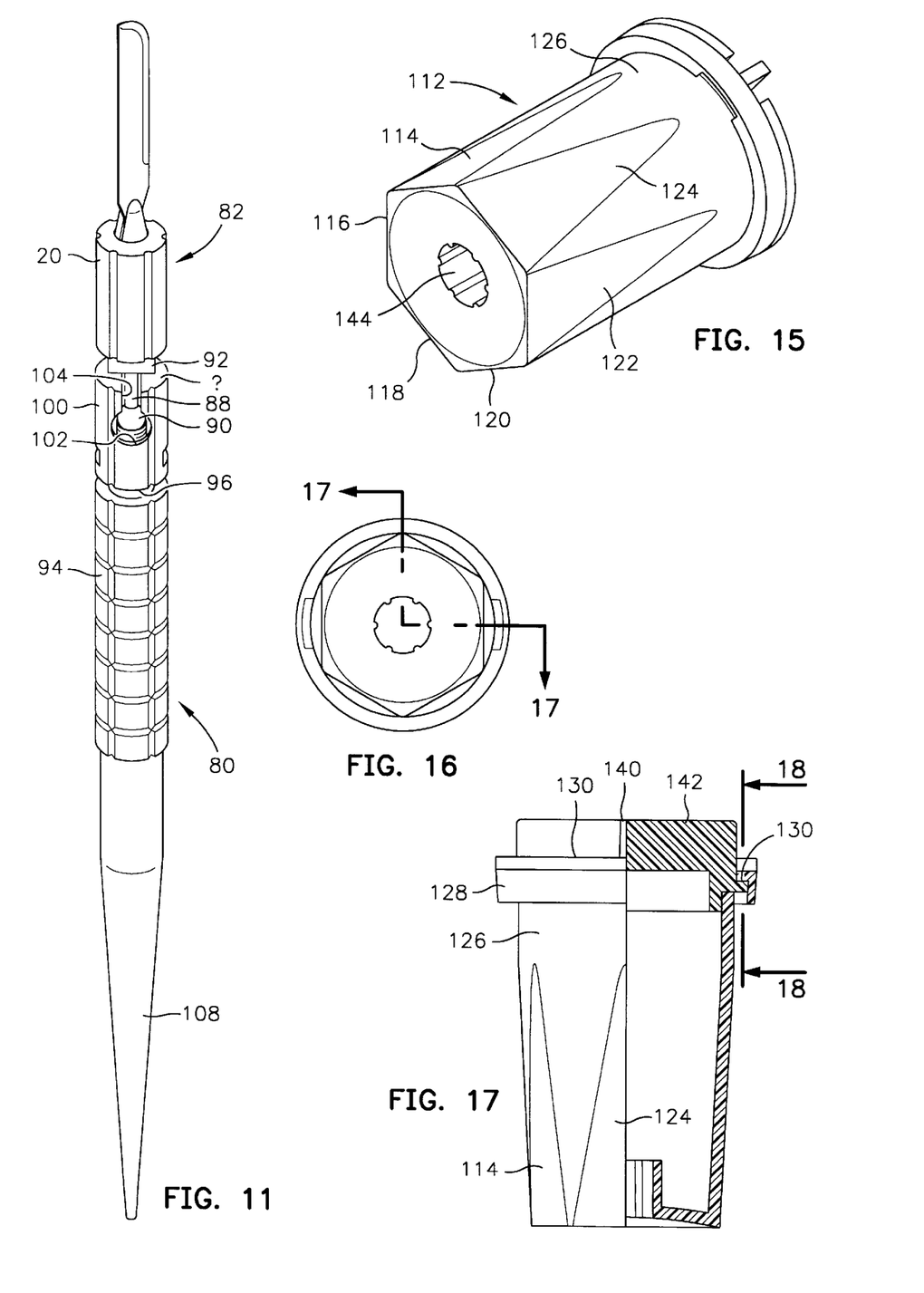
FIG. 11 is a view like FIG. 1 of the handle assembly of an alternate embodiment of the present invention.
FIGS. 15–19 are views of the wrench and holder or cover.
Figures 12, 18, 19:
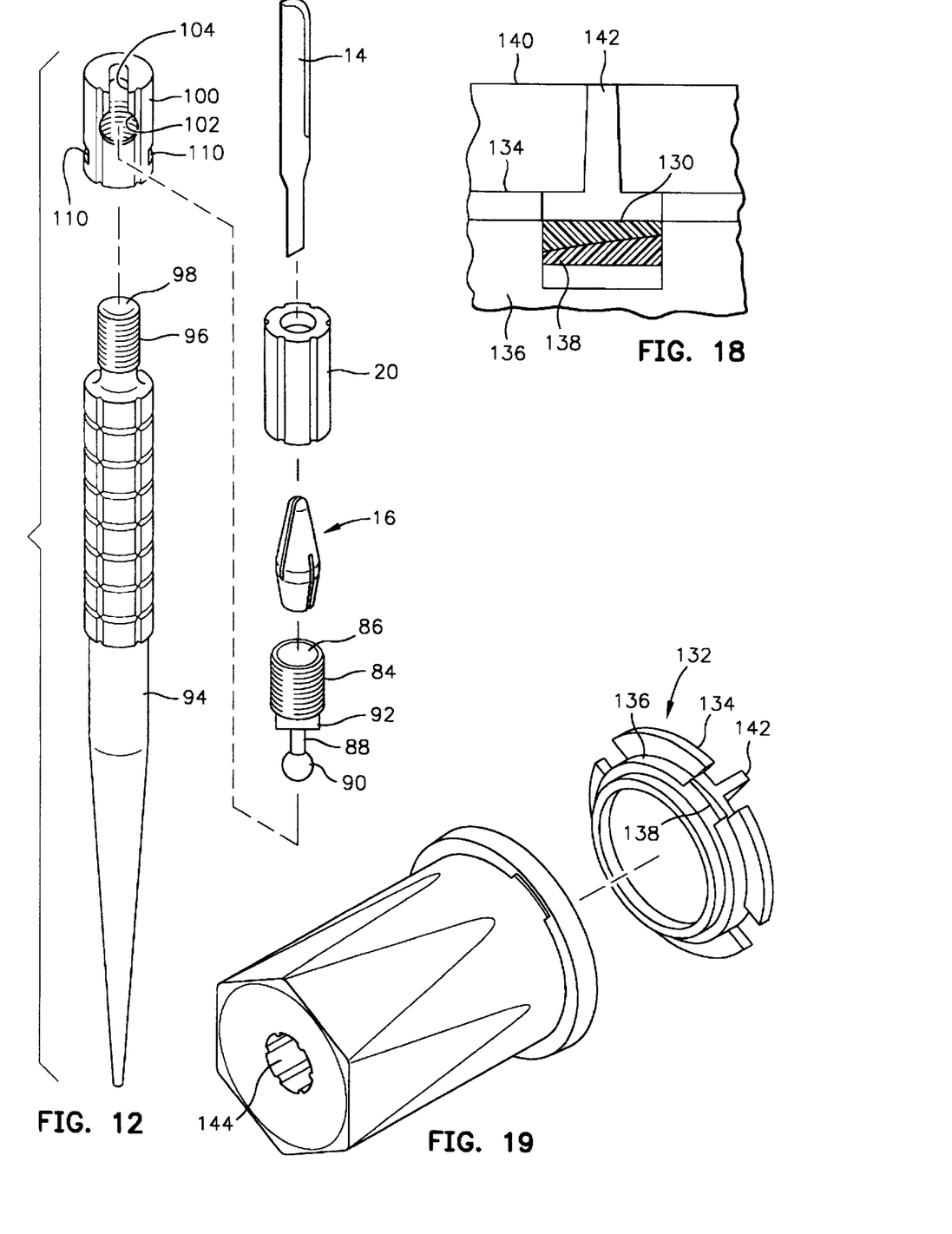
FIGS. 12–14 are other views of the alternate embodiment.

Referring now to FIGS. 11 and 12 of the drawings an alternate embodiment of the invention wherein the handle has a swivel head is illustrated. As illustrated, the blade mounting assembly is identical to that of the prior invention but incorporated in a swivel head designated generally by the numeral 82. The swivel head comprises a cylindrical body member 84 having a threaded cylindrical outer surface and a central bore 86 for receiving the collet. The opposite end of the body member 84 includes a shank 88 having an enlarged spherical tip 90 on the outer end thereof. A wrench engaging surface 92 is provided at the intersection of the shank 88 and the main body 84 to enable torque to be applied to the head.

Figure 13:
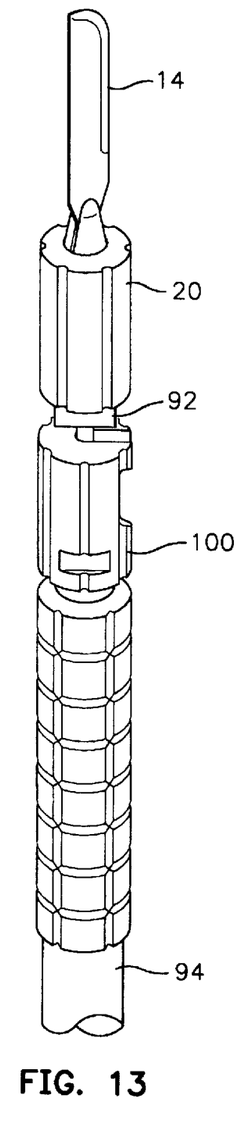

The swivel head is mounted on one end of an elongated handle 94. The elongated handle is provided with an axially extending threaded shank 96 having a semi-spherical socket 98 which engages the sphere 90. The term semi-spherical as used herein is intended to mean a portion of a sphere less than spherical whether true semi-spherical or less. A sleeve 100 has a threaded bore for threadably engaging the shank 96 and includes a transverse bore 102 intersected by an axially extending slot 104 for receiving the elongated shank 88 and spherical tip 90. The intersection of the transverse bore 102 and the slot 104 forms a recess in the sleeve for capturing the spherical tip 90 between the end of the shank 96 of the handle 94. The transverse bore 102 is large enough to receive the spherical tip 90, whereas the slot 104 is large enough for the shank 88 but not for the spherical tip 90. Thus, in this embodiment the swivel head can be aligned with the handle 94 as shown in FIGS. 11 and 131, or it can be tilted and secured in a selected angle between alignment as shown and 90° or right-angle to the handle 94.

Figure 14:
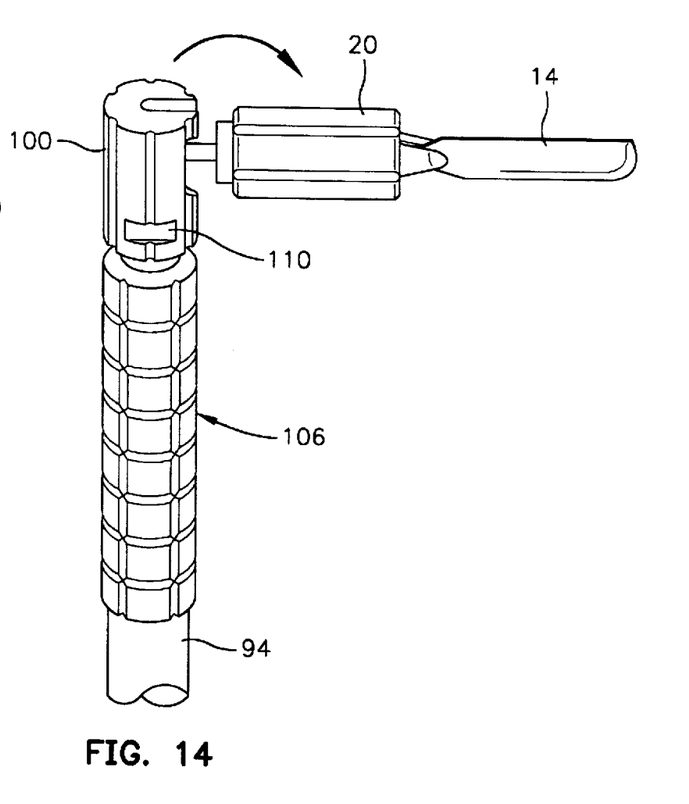

Referring to FIG. 14, the shank 88 pivots through the slot 104 from coaxial with the handle to the selected angular position up to 90 degrees relative to the axis of the handle. Thus, the knife blade can be positioned at any angle relative to the axis of the handle up to 90° thereto. In addition, the knife blade may be rotated about the axis of the retaining assembly and sleeve 20, such that in the 90° position to the handle the cutting edge itself may be aligned at a selected angle within a full 360° turn. The swiveling of the head and the rotation of the head for alignment of the knife blade cutting edge within the 360° position is achieved by loosening the sleeve 100 positioning the blade as desired and tightening the sleeve down against the spherical tip 90.

The handle 94 is preferably formed with a cylindrical area 106 having a cross-pattern of grooves forming a checkerboard pattern for ease of grip of the handle. The handle forms an elongated tapered smooth section 108 tapering down to substantially a point. This provides a pin-like holder for holding and manipulating a cutting blade. The sleeve 100 is provided with opposing flats 110 for engagement with a wrench.

Referring now to FIGS. 15 to 19 there is illustrated an alternate embodiment of the combined wrench and protective cover designated generally by the numeral 112. This embodiment has been modified to make it more convenient by providing an easier gripping surface and an easier and more convenient closure for the protective cover or container. As illustrated, the combined wrench and holder or cover 112 is a generally cylindrical container with a substantially hexagonal bottom section with flat surfaces 114, 116, 118, 120, 122, and 124 diverging upward to a circular section at 126 with a flared rim 128 with an upstanding skirt. The interior of the rim 128 is formed with wedge or ramp shaped latch members only one of which 130 is shown positioned around the periphery thereof. These latch members are preferable two to four in number and are wedge shaped to receive like members or a cover or closure.

The cover for the unit designated generally at 132 is formed as a notched disk 134 having a downwardly depending skirt 136 with latching members only one of which 138, is shown. These latching members on the closure are adapted for engaging the respective latch members on the inside of the container barrel upon rotation of the closure member. The notches in the rim are directly above the latching members on the downwardly depending skirt and are formed to provide ease of molding of the structure.

The top of the closure is formed with an axially projecting cross bars 140 and 142 forming a handle to enable the closure to be grasped and turned with the fingers. This provides a more convenient and easier to use combined wrench and protective cover for the blades. The wrench portion is formed substantially identical to the prior embodiment with a spliced bore 144 for engagement of the splices or ribs on the sleeves 20 and 100.

In view of the above description, it is possible that other modifications and improvements will occur to those skilled in the art which are within the scope of the appended claims. Therefore, this invention is not to be limited in any way except by the appended claims.

What is claimed is:

1. A handle assembly having a swivel head for detachably holding a blade, the assembly comprising:

a elongated handle having a proximal end and a distal end, said proximal end formed with a threaded shank having a hemispherical socket at the end thereof;

a sleeve having a threaded bore at one end for threadably mounting on said threaded shank, said sleeve having an open slot extending from the other end to intersection of said threaded bore and partially along the length thereof;

a blade mounting head comprising a threaded cylindrical body having a shank extending from one end, said shank adapted for receipt in said open slot and having a spherical tip for receipt in said threaded bore and engagement with said sleeve and said semi-spherical socket, said body adapted for swiveling on said spherical tip in said socket and slot, an axial bore extending coaxial of said threaded cylindrical body from the other end;

an elongated collet having a longitudinal axis and inner walls surrounding an axial passage and first and second opposite ends, the collet having a first longitudinal slit extending from the first end for receiving a blade into the axial passage and forming a first set of jaws that are compressible for gripping opposing sides of the blade, said collet adapted for receipt in said axial bore; and an elongated retaining sleeve member having first and second opposite open ends and a longitudinal axis with a longitudinal inner bore, the retaining member threadably mounted on said head and being configured to secure the collet and apply a compressive force to the collet for gripping a blade.

2. The handle assembly of claim 1, wherein said swivel head is selectively securable at selected angles up to 90 degrees with respect to the axis of said shaft.

3. The handle assembly of claim 2, wherein a blade secured in said head is selectively positionable at any selected angle about the axis of said head.

4. The handle assembly of claim 2, wherein said elongated handle has a generally cylindrical portion adjacent said proximal end and tapers to a smaller diameter at said distal end.

5. The combination of claim 4, wherein said sleeve includes a transverse bore intersecting said threaded bore at the intersection of said slot.

6. The combination of claim 5, wherein said transverse bore has a diameter large enough for passage of said spherical tip.

7. The combination of claim 4, wherein the retaining sleeve of the swivel head assembly has an outside spliced surface.

8. The combination of claim 7 further comprising a combined generally cylindrical wrench and protective covering having a spliced bore at one end to match the corresponding splices of the retaining member so that twisting the wrench rotates the retaining sleeve.

9. The combination of claim 4, further comprising a combined wrench and protective shield member's body comprises a first cylindrical portion having a first diameter and a second cylindrical portion having a second diameter, wherein the first cylindrical portion extends from the first end of the combined wrench and protective shield member to the beginning of the second cylindrical portion that extends to the second end of the combined wrench and protective shield member and the diameter of the second portion is greater than the diameter of the first portion.

10. The handle assembly of claim 1, wherein the retaining member has a threaded portion in the internal passage.

11. The handle assembly of claim 10, wherein the handle has a threaded portion at the first end for receiving the threaded portion of the retaining member.

12. A handle assembly having a swivel head for detachably holding a blade in selected angular positions relative to the handle, the assembly comprising:
a elongated handle having a proximal end and a distal end, said proximal end formed with a threaded shank having a hemispherical socket at the end thereof;
a sleeve having a threaded bore at one end for threadably mounting on said threaded shank, said sleeve having a transverse bore intermediate the ends thereof and an open slot extending from the other end to intersection of said transverse bore;
a blade mounting head comprising a threaded cylindrical body having a shank extending from one end, said shank adapted for receipt in said open slot and having a spherical tip for receipt in said threaded bore and engagement with said sleeve and said semi-spherical socket, said body adapted for swiveling on said spherical tip in said socket and slot, an axial bore extending coaxial of said threaded cylindrical body from the other end;
an elongated collet having a longitudinal axis and inner walls surrounding an axial passage and first and second opposite ends, the collet having a first longitudinal slit extending from the first end for receiving a blade into the axial passage and forming a first set of jaws that are compressible for gripping opposing sides of the blade, said collet adapted for receipt in said axial bore; and
an elongated retaining sleeve member having first and second opposite open ends and a longitudinal axis with a longitudinal inner bore, the retaining member threadably mounted on said head and being configured to secure the collet and apply a compressive force to the collet for gripping a blade.

13. The handle assembly of claim 12, wherein said swivel head is selectively securable at selected angles up to 90 degrees with respect to the axis of said shaft.

14. The handle assembly of claim 12, wherein a blade secured in said head is selectively positionable at any selected angle about the axis of said head.

15. The handle assembly of claim 12, wherein said elongated handle has a generally cylindrical portion adjacent said proximal end and tapers to a smaller diameter at said distal end.

16. The combination of claim 12, wherein said transverse bore has a diameter large enough for passage of said spherical tip.

17. The combination of claim 12, wherein the retaining sleeve of the swivel head assembly has an outside spliced surface.

18. The handle assembly of claim 12, wherein said collet is an elongated substantially conical collet having a longitudinal axis and inner walls surrounding an axial passage and first and second opposite ends, the collet having a first longitudinal slit forming a first set of jaws that are extending from the first end for receiving a blade into the axial passage and forming a first set of jaws that are compressible for gripping opposing sides of the blade, and further having a second longitudinal slit extending from the second end and forming a second set of jaws that are compressible for allowing the inner walls to grip opposing edges of the blade wherein the first longitudinal slit and the second longitudinal slit each extend from the respective first and second opposite ends such that the span of each slit overlaps the span of the other slit, wherein the first longitudinal slit is angularly displaced relative to the longitudinal axis and is offset by an angle from the second longitudinal slit; and
said retaining sleeve having first and second opposite open ends and a longitudinal axis with a longitudinal inner passage, the retaining member mounted at the first end of the handle and being configured to secure the collet and apply a compressive force to the collet.

19. The handle assembly of claim 16, further comprising a combined wrench and protective shield member's body comprises a first cylindrical portion having a first diameter and a second cylindrical portion having a second diameter, wherein the first cylindrical portion extends from the first end of the combined wrench and protective shield member to the beginning of the second cylindrical portion and forms a spliced coupling, the second cylindrical portion extends to the second end of the combined wrench and protective shield member and the diameter of the second portion is greater than the diameter of the first portion and has an open end, and a releasible latchable cover mounted over said open end.

20. A handle assembly having a swivel head for detachably holding a blade in selected angular positions relative to the handle, the assembly comprising:
a elongated handle having a proximal end and a distal end, said proximal end formed with a threaded shank having a hemispherical socket at the end thereof, said elongated handle having a generally cylindrical portion adjacent said proximal end and tapering to a smaller diameter at said distal end;
a sleeve having a threaded bore at one end for threadably mounting on said threaded shank, said sleeve having a transverse bore intermediate the ends thereof and an open slot extending from the other end to intersection of said transverse bore;
a blade mounting head comprising a threaded cylindrical body having a shank extending from one end, said shank adapted for receipt in said open slot and having a spherical tip for receipt in said threaded bore via said transverse bore and engagement with said sleeve and said semi-spherical socket, said body adapted for swiveling on said spherical tip in said socket and slot at selected angles up to 90 degrees with respect to the axis of said shaft, an axial bore extending coaxial of said threaded cylindrical body from the other end;
an elongated collet having a longitudinal axis and inner walls surrounding an axial passage and first and second opposite ends, the collet having a first longitudinal slit extending from the first end for receiving a blade into the axial passage and forming a first set of jaws that are compressible for gripping opposing sides of the blade, said collet adapted for receipt in said axial bore; and an elongated retaining sleeve member having first and second opposite open ends and a longitudinal axis with a longitudinal inner bore, said retaining sleeve having an outside spliced surface, said retaining sleeve threadably mounted on said head and being configured to secure the collet and apply a compressive force to the collet for gripping a blade, wherein a blade secured in said head is selectively positionable at any selected angle about the axis of said head.

* * * * *